United States Patent
Alonso et al.

(10) Patent No.: US 10,744,174 B1
(45) Date of Patent: Aug. 18, 2020

(54) COMPOSITION(S) AND METHOD(S) FOR TOPICALLY TREATING PAIN

(71) Applicants: Robert Alonso, North Hampton, NH (US); Lawrence G. Stoll, Clifton Park, NY (US)

(72) Inventors: Robert Alonso, North Hampton, NH (US); Lawrence G. Stoll, Clifton Park, NY (US)

(*) Notice: Subject to any disclaimer, the term of this patent is extended or adjusted under 35 U.S.C. 154(b) by 180 days.

(21) Appl. No.: 15/461,218

(22) Filed: Mar. 16, 2017

Related U.S. Application Data (60) Provisional application No. 62/309,354, filed on Mar. 16, 2016.

(51) Int. Cl.

| | |
|---|---|
| *A61K 36/28* | (2006.01) |
| *A61K 9/00* | (2006.01) |
| *A61K 47/20* | (2006.01) |
| *A61K 31/167* | (2006.01) |
| *A61K 47/38* | (2006.01) |
| *A61K 47/10* | (2017.01) |

(52) U.S. Cl.
CPC ............ *A61K 36/28* (2013.01); *A61K 9/0014* (2013.01); *A61K 31/167* (2013.01); *A61K 47/10* (2013.01); *A61K 47/20* (2013.01); *A61K 47/38* (2013.01)

(58) Field of Classification Search
None
See application file for complete search history.

(56) References Cited

U.S. PATENT DOCUMENTS

| | | | | |
|---|---|---|---|---|
| 4,851,442 A | * | 7/1989 | Watson | A61K 9/0014 514/553 |
| 5,081,157 A | * | 1/1992 | Pomerantz | A61K 9/006 424/434 |
| 5,093,133 A | * | 3/1992 | Wisniewski | A61K 9/0014 424/444 |
| 5,436,241 A | * | 7/1995 | Shin | A61K 9/0014 514/226.5 |
| 5,942,543 A | | 8/1999 | Ernst | |
| 6,280,750 B1 | * | 8/2001 | Roulier | A61K 8/0229 424/400 |
| 2015/0104485 A1 | | 4/2015 | Anton et al. | |

FOREIGN PATENT DOCUMENTS

| | | | |
|---|---|---|---|
| WO | 2013067591 | 5/2013 | |
| WO | WO-2015124616 A1 * | 8/2015 | ............ A61K 36/28 |

OTHER PUBLICATIONS

Jacobs (Podiatry Today (Jan. 15, 2013), 8 pages).*
Jeong (Nutrients (2017), vol. 9, 12 pages.*
Derry S, Wiffen PJ, Moore RA, Quinlan J., "Topical lidocaine for neuropathic pain in adults", Cochrane Database Syst Rev. Jul. 24, 2014;(7):CD010958. doi: 10.1002/14651858.CD010958.pub2.
"Vitamins and Minerals as a Treatment", Heel That Pain Rev. 2014., p. 1-3.
"Ketoprofen/Lidocaine/DMSO: Cream", Wedgewood Pharmacy, accessed Sep. 19, 2015, p. 1.
"Benzocaine, lidocaine, tetracaine, and dimethyl sulfoxide (KWICK Anesthetic Gel)", Public Citizen's Health Research Group, 2015, p. 1.
Moody, Mary Lynn, "Topical Medications in the Treatment of Pain", Pain Medicine News, Dec. 2010, p. 15-21.
Sobanko, Joseph F., Miller, Christopher J., and Alster, Tina S., "Topical Anesthetics for Dermatologic Procedures: A Review", Dermatologic Surgery, p. 1-13 2012.

* cited by examiner

*Primary Examiner* — Susan Hoffman
(74) *Attorney, Agent, or Firm* — GFD Patents LLC; Gerald F. Dudding (57) ABSTRACT

Pharmaceutically effective compositions and methods for topically treating pain due to swelling or inflammation of fascia, tendons, or ligaments in a patient in need of treatment, thereof. The pharmaceutically effective composition consists essentially of: 68.6-29.4 parts by weight of a pharmaceutically acceptable excipient; 40.0-50.0 parts by weight DMSO; 1.0-5.0 parts by weight of an anesthetic, wherein the anesthetic is advantageously characterized as containing only lidocaine; and 1.2-3.2 parts by weight of an anti-inflammatory in 100 parts by weight of the pharmaceutically effective composition. In one embodiment, the anesthetic is advantageously 4.0 parts by weight Lidocaine. In one embodiment, the pharmaceutically acceptable excipient is 48.0 parts by weight, DMSO is 45 parts by weight, anesthetic is advantageously 4.0 parts by weight Lidocaine, Echinaceas is 1.0 part by weight and Arnica is 1.0 part by weight, and the condition causing pain of the foot is Plantar Fasciitis.

11 Claims, 5 Drawing Sheets

100 topically applying the pharmaceutically effective composition at ambient temperature to a patient in need of treatment thereof. — 110

```
┌─────────────────────────────┐
│ incrementally adding isopropyl │
│ alcohol (IPA), dimethyl sulfoxide │
│ (DMSO), lidocaine, propylene │ ── 210
│ glycol (1,2 dihydroxy Propane), │
│ Echineras and Arnica are with │
│ mixing in a high shear mixer for 30 │
│ minutes, forming a solution.; and │
└─────────────────────────────┘
              │
              ▼
┌─────────────────────────────┐
│ incrementally adding │
│ hydroxypropyl cellulose NF (HPC) │
│ to the solution of step 210 with │ ── 220
│ continued mixing, resulting in a │
│ thickened mixture having a │
│ viscosity from about 9,000 – │
│ 21,000 cps at 20°C that may be │
│ used for topically treating foot │
│ pain due to swelling or │
│ inflammation of facia, tendons or │
│ ligaments of the foot in a patient │
│ in need of treatment. │
└─────────────────────────────┘
```

COMPOSITION(S) AND METHOD(S) FOR TOPICALLY TREATING PAIN

BACKGROUND

1.1 Field of the Invention

The present invention relates to compositions and methods of topically treating pain caused by swelling or inflammation of the fascia, ligaments or tendons of a mammal. Specifically, the present invention relates to compositions and methods of topically treating pain in the foot caused by swelling or inflammation of the fascia, ligaments or tendons of the foot of a person in need of treatment, thereof, e.g. plantar fasciitis.

1.2 Prior Art

Lidocaine may be topically applied to the skin as an anesthetic to reduce pain. Derry S. Wiffen, P J, Moore R A, and Quinlan J. Cochrane[1] reported twelve topical studies using a 5% medicated patch, a 5% cream, a 5% gel, and an 8% spray to treat pain. These 12 studies (totaling 508 participants) used comparisons with placebo or an active control. Six studies enrolled participants with moderate or severe postherpetic neuralgia, and the remaining studies enrolled different, or mixed, neuropathic pain conditions, including trigeminal neuralgia and postsurgical or post-traumatic neuralgia. There was no first or second tier evidence, and no pooling of data was possible for efficacy outcomes. Only one multiple-dose study reported a primary outcome of participants with ≥50% or ≥30% pain intensity reduction. Three single-dose studies reported participants who were pain-free at a particular time point, or had a 2-point (of 10) reduction in pain intensity. The two enriched enrolment, randomised withdrawal studies reported time to loss of efficacy. In all but one study, third tier (very low quality) evidence indicated that lidocaine was better than placebo for some measure of pain relief.

Therefore, there is a need for improved treatments of pain, e.g., pain caused by swelling or inflammation of the fascia, ligaments or tendons of a person in need of treatment.

BRIEF DESCRIPTION OF THE FIGURES

The features of the invention are set forth in the appended claims. The invention itself, however, will be best understood by reference to the following detailed description of an illustrative embodiment when read in conjunction with the accompanying drawings, wherein:

SUMMARY OF THE INVENTION

A first aspect of the present invention provides a pharmaceutically effective composition for topically treating pain due to swelling or inflammation of fascia, tendons or ligaments in a patient in need of treatment, thereof. The pharmaceutically effective composition consists essentially of: 68.6-29.4 parts by weight of a pharmaceutically acceptable excipient; 40.0-50.0 parts by weight DMSO; 1.0-5.0 parts by weight of an anesthetic, wherein the anesthetic is advantageously characterized as containing only lidocaine; and 1.2-3.2 parts by weight of an anti-inflammatory in 100 parts by weight of the pharmaceutically effective composition. In one embodiment, the composition contains 1.2-3.2 parts by weight of an anti-inflammatory selected from the group consisting of Echinaceas, Arnica, and combinations thereof. In one embodiment, the anesthetic is 4.0 parts by weight Lidocaine. In one embodiment, the pharmaceutically acceptable excipient is 48.0 parts by weight, DMSO is 45 parts by weight, anesthetic is 4.0 parts by weight Lidocaine, Echinaceas is 1.0 part by weight and Arnica is 1.0 part by weight, and the condition causing pain of the foot is Plantar Fasciitis.

A second aspect of the present invention provides a method for topically treating a condition causing pain due to swelling or inflammation of fascia, tendons, or ligaments of a patient in need of treatment thereof, comprising: topically applying a pharmaceutically effective composition at ambient temperature to a patient in need of treatment thereof. The pharmaceutically effective composition consists essentially of: 68.6-29.4 parts by weight of a pharmaceutically acceptable excipient; 40.0-50.0 parts by weight DMSO; 1.0-5.0 parts by weight of an anesthetic, wherein the anesthetic is advantageously characterized as containing only lidocaine; and 1.2-3.2 parts by weight of an anti-inflammatory in 100 parts by weight of the pharmaceutically effective composition.

DESCRIPTION OF THE EMBODIMENTS

Definitions:

Hereinafter, unless otherwise stated, the term "about" is defined as variations in amounts in either active compounds or excipients that would be considered bioequivalent by a regulatory agency such as the United States Food and Drug Administration (FDA) or other recognized regulatory agency, e.g. EMEA for Europe, the Middle East, and Africa.

Hereinafter, unless otherwise stated, the term 'pharmaceutically effective amount" of a compound or composition is an amount sufficient to contribute to the treatment, prevention, or reduction of a symptom or symptoms of a disease. Where recited in reference to a disease treatment, a "pharmaceutically effective amount" may also be referred to as a "therapeutically effective amount."

Hereinafter, unless otherwise stated, "A reduction of a symptom or symptoms" (and grammatical equivalents of this phrase) means decreasing of the severity or frequency of the symptom(s), or elimination of the symptom(s).

Hereinafter, unless otherwise stated, "a pharmaceutically acceptable carrier' or "pharmaceutically acceptable excipient" means a carrier or an excipient that is useful in preparing a pharmaceutical composition that is generally safe, non-toxic and neither biologicaly nor otherwise undesirable, and includes a carrier or an excipient that is acceptable for vetinary use as well as human pharmaceutical use. In addition, "a pharmaceutically acceptable carrier' or "pharmaceutically acceptable excipient" is defined as an inert substance with regard to a therapeutically or pharmaceutically effective composition, which is part the composition of the present teachings to adjust viscosity, bulk, or remove undesirable nucleophiles that may decompose the pharmaceutically effective composition by chemical reaction.

Hereinafter, unless otherwise stated, "a pharmaceutically acceptable carrier/excipient" as used in the specification and claims includes both one and more than one such excipient.

Hereinafter, unless otherwise stated, the term "Eschinaceas" is defined as a group of herbaceous flowering plants in the daisy family, where echinaceas contains active substances that boost immune function, relieve pain, reduce inflammation, and have favorable hormonal, antiviral, and antioxidant effects.

Hereinafter, unless otherwise stated, the term "Arnica" is defined as the perennial Arnica Montana, a yellow-orangish flower which grows on the mountains of Europe and Siberia. It's sometimes called the "mountain daisy," because its color and petals look like the daisy. Creams and ointments made from the flower head can be used to treat muscle soreness and aches, bruising, joint pain and swelling, and inflammation.

Hereinafter, unless otherwise stated, the term "plantar fasciitis" is defined as a condition caused by swollen or inflamed plantar fascia.

Figure 1:
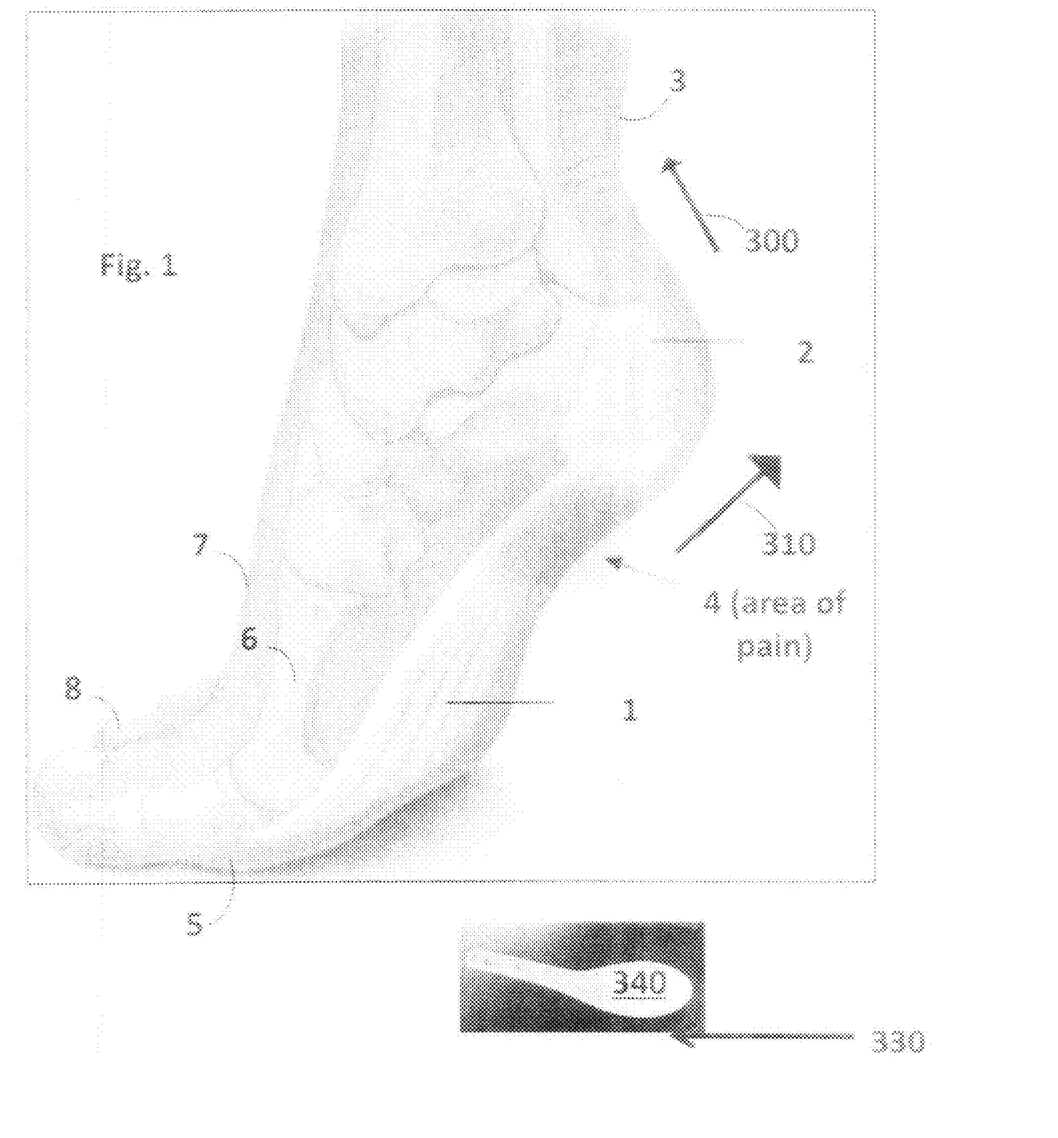
FIG. 1 depicts a front elevation view of the anatomy of the human foot, in accordance with embodiments of the present invention.

FIG. 1 shows front elevation view plantar fascia 1, the thick tissue on the bottom of the foot 7. It connects the heel bone 2 to the toes 8 and creates the arch 4 of the foot 7. Plantar fasciitis may be characterized by swelling or inflammation of the plantar fascia 1. Plantar fasciitis may occur when the thick band of tissue on the bottom of the foot 7 is overstretched or overused. This can be painful and make walking more difficult.

Having one or more of the following characteristics increases the probability of plantar fasciitis:
  Have foot arch problems (both flat feet and high arches)
  Run long distances, downhill or on uneven surfaces
  Are obese or gain weight suddenly
  Have a tight Achilles tendon (the tendon connecting the calf muscles to the heel)
  Wear shoes with poor arch support or soft soles
  A change in activities Plantar fasciitis is seen in both men and women. However, it most often affects active men ages 40-70.

Symptoms

The most common symptom of plantar fasciitis are pain and stiffness in the bottom of the heel. The heel pain may be dull or sharp. The bottom of the foot may also ache or burn.
  The pain is often worse:
  In the morning when taking first steps
  After standing or sitting for awhile
  When climbing stairs
  After intense activity The pain may develop slowly over time, or come on suddenly after intense activity.

Exams and Tests

The health care provider will perform a physical exam. This may show:
  Tenderness on the bottom of the foot
  Flat feet or high arches
  Mild foot swelling or redness
  Stiffness or tightness of the arch in the bottom of the foot.
X-rays may be taken to rule out other problems.

Treatment

The initial treatment is usually orthotics of some sort to deal with the mechanical problem and pain medication (such as Acetaminophen (Tylenol) or ibuprofen (Advil, Motrin)) to reduce pain and inflammation while the mechanical problem is being corrected. However, these methods provide pain tolerance, not pain relief. Therefore, there is a present need for improved treatments of pain caused by swelling or inflammation of the fascia, ligaments or tendons of a person in need of treatment.

A. Composition and Properties of the Composition for Topically Treating Foot Pain Due to Swelling or Inflammation of Fascia, Tendons or Ligaments of the Foot in a Patient in Need of Treatment In one embodiment, a composition is described in Table 1, consists of 68.6-29.4 parts by weight of a pharmaceutically acceptable excipient, 40-50 parts by weight DMSO, 1.0-5.0 parts by weight of an anesthetic, where the anesthetic is advantageously characterized as containing only lidocaine, and 1.2-3.2 parts by weight of an anti-inflammatory.

In one embodiment, the anti-inflammatory is selected from the group consisting of Enchinaceas, Arnica and combinations thereof.

In one embodiment, the anti-inflammatory is 0.6 parts by weight Enchinaceas and 0.6 parts by weight Arnica.

In one embodiment, the pharmaceutically acceptable excipient comprises 0.6-1.6 parts by weight hydroxypropyl cellulose HPC, resulting in a viscosity of the composition being from about 18,000 cps to about 42,000 cps at 20° C.

In an embodiment, the pharmaceutically acceptable excipient is selected from the group of excipients consisting essentially of DMSO, isopropyl alcohol, propylene glycol (PG), ethylene glycol (EG), polypropylene glycol (PPG), diethylene glycol monosubstituted ether (DGMSE), BHT, glycerin, propylene glycol, transcutol, triethanolamine, hydroxypropyl cellulose, nitro cellulose and hydroxypropyl Cellulose (NF), hydroxypropyl cellulose (HPC), and combinations thereof.

In one embodiment, the pharmaceutically acceptable excipient comprises 0.6-1.6 parts by weight hydroxypropyl cellulose HPC, resulting in a viscosity of the composition being from about 18,000 cps to about 42,000 cps at 20° C.

In an embodiment, the pharmaceutically acceptable excipient is selected from the group of excipients consisting essentially of DMSO, isopropyl alcohol, propylene glycol (PG), ethylene glycol (EG), polypropylene glycol (PPG), diethylene glycol monosubstituted ether (DGMSE), BHT, glycerin, propylene glycol, transcutol, triethanolamine, hydroxypropyl cellulose, nitro cellulose and hydroxypropyl Cellulose (NF), hydroxypropyl cellulose (HPC), and combinations thereof.

Alternatively, the pharmaceutically acceptable excipient includes Water, Ethanol, Isopropyl, cetyl, stearyl, cetearyl, or lanolin alcohol are preferred pharmaceutically acceptable excipients for dissolving or taking up the pharmaceutically effective composition of the present invention. Alternatively, for example, for topical formulations, pharmaceutically acceptable excipients may comprise solvents, emollients, humectants, preservatives, emulsifiers, and pH agents. Suitable solvents include acetone, glycols, polyurethanes, and others known in the art. Suitable emollients include mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art.

The pharmaceutically acceptable excipient for the control composition (4 wt. % Lidocaine) used in Examples 4 and 5 for patient studies listed in Tables 4 and 5 includes Purified Water, Aloe Vera Gel, Isopropyl Myristate, Polyacrylamide, C13 & 14 Isoparaffin Laureth-7, Propylene Glycol, Diazolidinyl Urea, Methylparaben, Carbomer, Propylparaben, and Triethanolamine.

In one embodiment, the anesthetic is in the range of 3.0 to 5.0 parts by weight Lidocaine.

In one embodiment, the anesthetic is 4.0 parts by weight Lidocaine, Echinaceas is 1.0 part by weight and Arnica is 1.0 part by weight.

The excipient may contain 1.0 part hydroxypropyl cellulose NF, such that the viscosity of the composition is in the range about 18,000 cps to about 42,000 cps at 20° C.

In one embodiment, a composition of the present invention is listed in Table 2, consists of 68.6-29.4 parts by weight of a pharmaceutically acceptable excipient, 40-50 parts by weight DMSO, 1.0-5.0 parts by weight of an anesthetic, wherein the anesthetic is advantageously characterized as containing only lidocaine, and 1.2-3.2 parts by weight of an anti-inflammatory.

In one embodiment, the pharmaceutically acceptable excipient is selected from the group of excipients consisting essentially of DMSO, isopropyl alcohol, propylene glycol (PG), ethylene glycol (EG), polypropylene glycol (PPG), diethylene glycol monosubstituted ether (DGMSE), BHT, glycerin, propylene glycol, transcutol, triethanolamine, hydroxypropyl cellulose, nitro cellulose and hydroxypropyl Cellulose (NF), hydroxypropyl cellulose (HPC), and combinations thereof.

In one embodiment, the pharmaceutically effective composition is advantageously 48.0 parts by weight pharmaceutically acceptable excipient, DMSO is 45 parts by weight, anesthetic is 4.0 parts by weight Lidocaine, Echinaceas is 1.0 part by weight and Arnica is 1.0 part by weight.

In an embodiment, the pharmaceutically acceptable excipient comprises 14 parts by weight to 32 parts by weight of propylene glycol.

B. Preparation of the Compositions for Topically Treating Foot Pain Due to Swelling or Inflammation of Fascia, Tendons or Ligaments of the Foot in a Patient in Need of Treatment The compositions for topically treating foot pain due to swelling or inflammation of fascia, tendons or ligaments of the foot in a patient in need of treatment, thereof, may be prepared by mixing the components listed in Table 1 and Table 2, infra, according to the following general method 200, depicted in FIG. 3, and described infra.

Figure 3:
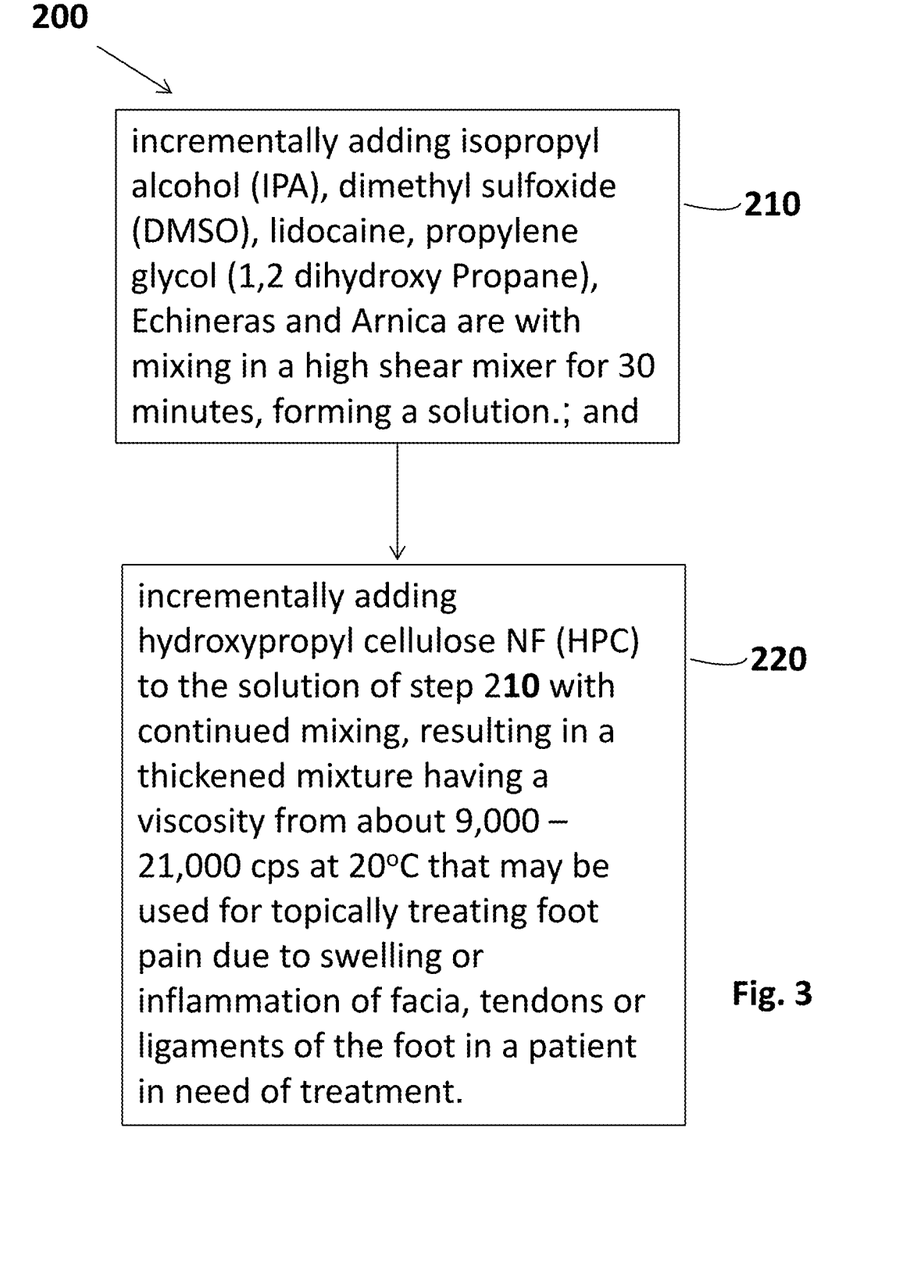
FIG. 3 depicts a flow diagram of a method 200 for preparing the composition of Table 1, 2 and 3, in accordance with embodiments of the present invention.

In step 210 of the method 200, isopropyl alcohol (IPA), dimethyl sulfoxide (DMSO), lidocaine, propylene glycol (1,2 dihydroxy Propane), Echinaceas and Arnica are incrementally added with mixing in a high shear mixer for 30 minutes, forming a solution. In step 210 of the method 200, hydroxypropyl cellulose NF (HPC) is incrementally added to the solution of step 210 with continued mixing, resulting in a thickened mixture having a viscosity from about 9,000-21,000 cps at 20° C. that may be used for topically treating foot pain due to swelling or inflammation of fascia, tendons or ligaments of the foot in a patient in need of treatment, thereof.

The following examples are illustrative of the compositions of the present teachings, and are not intended in any way to limit their scope.

C. Method of Use

Figure 2:
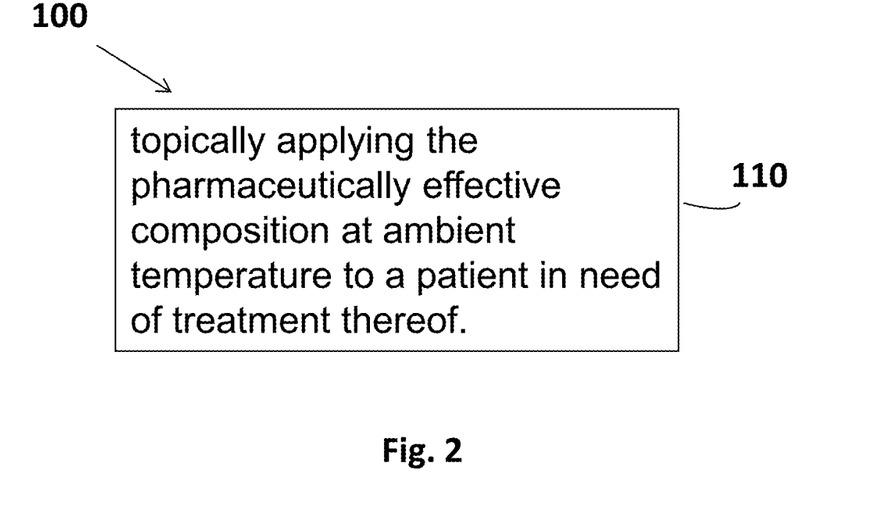
FIG. 2 depicts a flow diagram of a method 100 for topically treating foot pain due to swelling or inflammation of fascia, tendons, or ligaments in the foot of a patient in need of treatment thereof, in accordance with embodiments of the present invention.

FIG. 2 depicts a flow diagram of a method 100 for topically treating foot pain due to swelling or inflammation of fascia, tendons, or ligaments in the foot of a patient in need of treatment thereof. The method 100 consists of a step 110, topically applying the pharmaceutically effective composition at ambient temperature to a patient in need of treatment thereof. The pharmaceutically effective composition consists essentially of: 68.6-29.4 parts by weight of a pharmaceutically acceptable excipient; 40.0-50.0 parts by weight DMSO; 1.0-5.0 parts by weight of an anesthetic, wherein the anesthetic is advantageously characterized as containing only lidocaine; and 1.2-3.2 parts by weight of an anti-inflammatory in 100 parts by weight of the pharmaceutically effective composition. The inventors report that treatment of a patient experiencing pain due to swelling or inflammation of fascia, tendons, or ligaments in the foot using the method 100 results in a greater reduction of pain than would be achieved if the pain were treated using a control composition containing only lidocaine in the same concentration.

In an embodiment of the method, the pain is caused by swelling or inflammation of the plantar fascia and the condition is Plantar fasciitis. In another embodiment, the pain is selected from the group consisting of bilateral arch pain, right arch pain, right arch and metatarsal pain, bilateral arch and heel pain, right arch and heel pain, left lateral heel and metatarsal pain, right arch and medial forefoot pain, moderate arch and heel pain, arch and forefoot pain and itching.

The following examples are illustrative of the pharmaceutically effective compositions for topically treating foot pain due to swelling or inflammation of fascia, tendons or ligaments of the foot of the present teachings, and are not intended in any way to limit their scope.

D. Examples

Examples 1-3: Preparation of the Composition for Topically Treating Foot Pain Due to Swelling or Inflammation of Fascia, Tendons, or Ligaments in the Foot of a Patient in Need of Treatment Thereof.

Example 1

The pharmaceutically effective composition for topically treating foot pain due to swelling or inflammation of fascia, tendons or ligaments of the foot in a patient in need of treatment, thereof, may be prepared by mixing, according to steps 210 and 220 of the method 200: 68.6-29.4 parts by weight of a pharmaceutically acceptable excipient; 40-50 parts by weight DMSO; 1.0-5.0 parts by weight of an anesthetic, wherein the anesthetic is advantageously characterized as containing only lidocaine; 0.6-1.2 parts by weight Echinaceas from the genus Echinaceas; and 0.6-1.2 parts by weight Arnica. The components/compositions are provided in Table 1 that follows.

TABLE 1

Unit/Batch Composition

| Ingredient | Wt %[a] |
|---|---|
| Isopropyl Alcohol [b] | 15.0-35.0 |
| Propylene Glycol (1,2 dihydroxy Propane) [c] | 13.8-32.2 |
| Dimethylsulfoxide (DMSO) | 40.0-50.0 |
| Hydroxypropylcellulose NF 1500 CPS | 0.6-1.6 |
| Lidocaine | 1.0-5.0 |
| Echinaceas | 0.6-1.2 |
| Arnica | 0.6-1.2 |

[a] Slight overages of the drug substances may be used as required to offset losses during manufacture.
[b] Available from Nexeo Solutions, Rensselaer, NY 12144.
[c] Available from Kraft Chemical, Melrose Park, IL 60160.

Example 2

In an alternative formulation, the pharmaceutically effective composition for topically treating foot pain due to swelling or inflammation of fascia, tendons or ligaments of the foot in a patient in need of treatment, thereof, may be prepared by mixing, according to steps 210 and 220 of the method 200: 68.6-29.4 parts by weight of a pharmaceutically acceptable excipient; 40-50 parts by weight DMSO; 3.0-5.0 parts by weight of an anesthetic, wherein the anesthetic is advantageously characterized as containing only lidocaine; and 1.2-3.2 parts by weight Echinaceas from the genus Echinaceas and Arnica. The components/compositions are provided in Table 2 that follows.

TABLE 2

Unit/Batch Composition

| Ingredient | Parts by weight[a] |
|---|---|
| Isopropyl Alcohol [b] | 15.0-35.0 |
| Propylene Glycol (1,2 dihydroxy Propane) [c] | 13.8-32.2 |
| Dimethylsulfoxide (DMSO) | 40.0-50.0 |
| Hydroxypropylcellulose NF 1500 CPS | 0.6-1.6 |
| Lidocaine | 3.0-5.0 |
| Echinaceas[g] and Arnica | 1.2-3.2 |

[a] Slight overages of the drug substances may be used as required to offset losses during manufacture.
[b] Available from Nexeo Solutions, Rensselaer, NY 12144.
[c] Available from Kraft Chemical, Melrose Park, IL 60160.

Example 3

In an alternative formulation, the pharmaceutically effective composition for topically treating foot pain due to swelling or inflammation of fascia, tendons or ligaments of the foot in a patient in need of treatment, thereof, may be prepared by mixing, according to steps 210 and 220 of the method 200: 49 parts by weight of a pharmaceutically acceptable excipient; 45.0 parts by weight DMSO; 4.0 parts by weight of an anesthetic, wherein the anesthetic is advantageously characterized as containing only lidocaine; and 1.0 part each of Echinaceas from the genus Echinaceas and Arnica. The components/compositions are provided in Table 3 that follows.

TABLE 3

Unit/Batch Composition

| Ingredient | Parts by weight[a] |
|---|---|
| Isopropyl Alcohol [b] | 25.0 |
| Propylene Glycol (1,2 dihydroxy Propane) [c] | 23.0 |
| Dimethylsulfoxide (DMSO) | 45.0 |
| Hydroxypropylcellulose NF 1500 CPS | 1.0 |
| Lidocaine | 4.0 |
| Echinaceas | 1.0 |
| Arnica | 1.0 |
| Total | 100 |

[a] Slight overages of the drug substances may be used as required to offset losses during manufacture.
[b] Available from Nexeo Solutions, Rensselaer, NY 12144.
[c] Available from Kraft Chemical, Melrose Park, IL 60160.

Example 4

Instructions For Topically Treating Foot Pain Due to Swelling or Inflammation of Fascia, Tendons or Ligaments of the Foot in a Patient in Need of Treatment, Thereof.

To Apply:

FIG. 1 depicts a front elevation view of the plantar fascia 1 running along the bottom of a person's foot 7. Potentially painful areas such as along the plantar fascia 1, the heel 2, Achilles 3, arch 4, forefoot 5 having metatarsal bones 6 are shown. Squeeze out a pea size drop of the composition listed in Tables 1-3 onto the flat bottom portion 330 of the small white spoon 340 and spread evenly onto all painful areas such as heel, achilles and flat bottom of the patient's foot. Spread the composition of Table 3 in an area about ½ to one inch wider than the actual painful area. Using a gentle circular motion with the spoon, gently apply and massage the composition of Table 3 into the skin for a period of 30-60 seconds using the bottom portion 330 of the spoon 340. Increased pressure to be applied in a slow and gradual manner to personal comfort.

Alternatively, the composition of Tables 1-3 may be topically applied to the pain area and massaged into the skin using the pads of the fingers, fingertips or palm of one's hand.

In additional to using the spoon in a circular fashion, you can also massage in an uni-direction manner, not back and forth, just one direction from toes toward heel, according to arrow 310 and from back of heel up the Achilles towards the knee, according to arrow 300.

Although the composition of Tables 1-3 is totally safe, wash your hands and the spoon after applying the pain reducing gel. Allow for about 3 minutes or until the gel is dry on the skin before putting on socks and shoes and beginning to stand and walk.

*Why Use Spoon Applicator?

It is well accepted that massage to a painful area feels good and is medically therapeutic. There is another technique of traditional Asian medicine called Gua sha, that we can combine with self-massage and the use of the composition of Tables 1-3. Gua sha is defined as instrument-assisted press-stroking of a lubricated area of the body surface to promote an increase in blood flow, thus lessening the discomfort in the painful area.

Combining the therapeutic effects of the composition of Tables 1-3, self-message and traditional Asian wisdom provides maximum pain reducing effects.

Example 5

Pain Reduction Study Over a Two-Week Period Using an Absolute Visual Analogue Scale (AVAS) as a Measure of Pain Intensity.

A study of pain reduction based on topically treating foot pain due to swelling or inflammation of fascia, tendons or ligaments of the foot in a patient in need of treatment, thereof, was conducted for a test group and a control group over a two-week period using an absolute visual analogue scale (AVAS) as a measure of pain intensity.

A total of 20 patients, with a high percentage documenting plantar foot pain, were followed in our practice from April 2015 to December 2015. Patients ranged in age from 31 to 76 years old. The first 10 patients (one patient was lost to follow-up) were exclusively treated with the composition listed in Table 3, supra, and the second 10 were treated with a generic topical lidocaine (4%). The patients were classified as either: plantar fascia pain (plantar fasciitis), or arch/heel/ other pain. Nine (9) out of the 19 evaluable patients (45%) experienced bi-lateral involvement. No other pharmaceutical treatments were provided; however, their existing prescription medicines and non-pharmaceutical treatments (supports/orthotics, etc.) were maintained during the study period. During the course of the study period, patients in the test group were instructed to use the composition listed in Table 3 and the patients in the control group were instructed to use the generic lidocaine (4%) every 8 hours or as needed, not to exceed every 4 hours. The patient was further instructed to maintain his/her use of orthotics or other devices that had previously been prescribed by our practice or from past practitioners. Patients were seen at baseline, 1 week and 2 weeks for evaluation and scoring using both visual analogue and numeric pain intensity scales.

Table 4, infra, lists average reduction in pain scale and average reduction in pain score (out of 10) from study initiation for the test group. In the test group, the composition described in Table 3 was used to topically treat foot pain most likely caused by swelling or inflammation of fascia, ligaments or tendons of the foot, e.g., plantar fascia, as in Example 4. Of the 10 patients experiencing pain who entered the study, patient (#4) and (#10) was disqualified by the investigator because patient (#4)'s pain was found to be caused by neuropathy instead of plantar fasciitis and patient (#10) did not complete the treatment. All patients except patient #4 were treated for plantar fasciitis.

Table 5, infra, lists average reduction in pain scale and average reduction in pain score (out of 10) from study initiation for the control group for comparison with Table 4. In the control group, a composition consisting of lidocaine 4%, the balance being Isopropyl Alcohol, Propylene Glycol (1,2 dihydroxy Propane), and Hydroxypropylcellulose NF 1500 CPS, but which did not contain DMSO, Echinaceas, or Arnica, was used to topically treat foot pain most likely caused by swelling or inflammation of fascia, ligaments or tendons of the foot, e.g., plantar fascia, as in Example 4.

Figure 4:
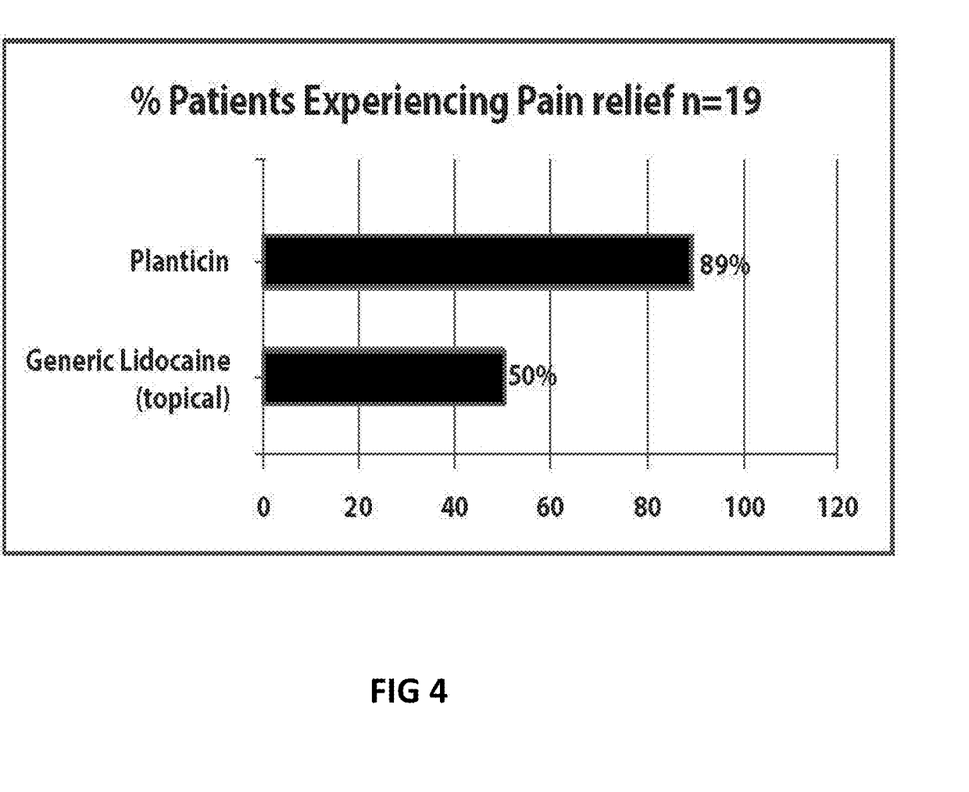
FIG. 4 depicts a bar chart comparing % Patients Experiencing Pain relief for the test group and the control group, in accordance with embodiments of the present invention.
Figure 5:
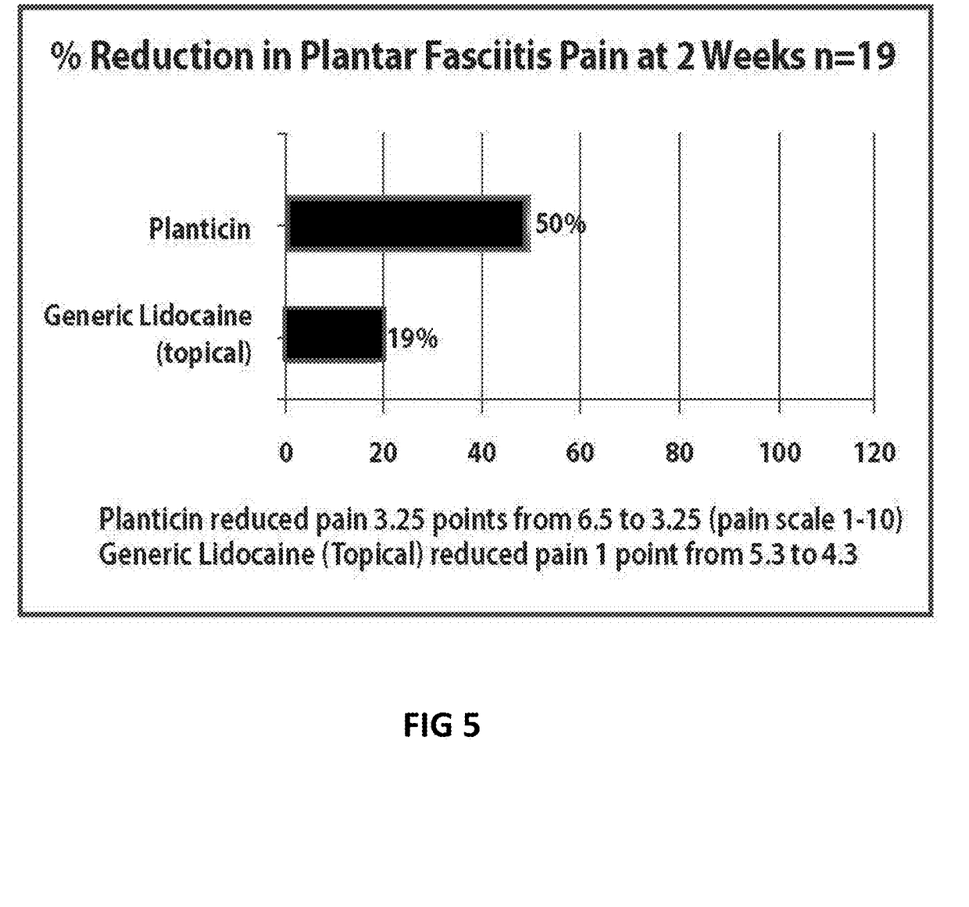
FIG. 5 depicts a bar chart comparing % Reduction in Plantar Fasciitis Pain for the test group and the control group, in accordance with embodiments of the present invention.

FIG. 4 provides a bar chart comparing % Patients Experiencing Pain relief for the test group and the control group. Of the 9 evaluable patients treated with the composition described in Table 3, 89% reported experiencing pain relief with an average reduction in pain intensity for plantar fascia/heel pain patients of 50% (baseline=6.5 and 2 weeks=3.25). Of the two neuropathic patients one responded well (66% reduction in pain intensity score) while the other patient had no change. In comparision, the generic lidocaine group experienced only a 19% reduction in their pain scores with an average 1-point reduction in pain intensity.

Of particular note was a patient (Subject 1, Table 4) with extensive arch and digital pain that also was complicated with elements of neuropathic pain. This patient had bi-lateral involvement and entered the study with pain intensity scores of 6. After 1 week of treatment with the composition described in Table 3 this patient reported 100% improvement in the digital pain and a 66% reduction in total pain intensity scores.

Based on our experience with these patients, we noted that to provide for maximum results there needed to be a period of time between applications of the composition described in Table 3 and putting on socks and shoe-gear. It was emphasized to patients the need to gently rub the composition described in Table 3 into the painful area and about one inch additionally around the area of maximum pain.

Although our small study was limited to only 19 evaluable patients, we were quite impressed with this new topical analgesic, the components of which are listed in Table 3, as per ease of use, effectiveness, and patients reporting they would pur chase when commercially available. There were little to no safety issues (minor erythema was noted when too much of the product was applied) and the product worked very well in most patients. The doctor reporting the results listed in Table 4 reported he believes the composition described in Table 3 offers an excellent alternative to other analgesics, particularly with topical prescription lidocaine and generic lidocaine preparations.

Reduction in Pain and Reduction in Pain Score after topically treating foot pain for the test group is listed in Table 4, infra, and after topically treating foot pain for a control group is listed in Table 5, infra. The Reduction in Pain and Reduction in Pain Score results support the conclusion that the compositions described in Table 3, and by extrapolation in Tables 1-2, were more effective for topically treating pain caused by swelling or inflammation of fascia, ligaments or tendons in the foot of a mammal, e.g., a person, than the control composition, containing Lidocaine (4%), the balance being Isopropyl Alcohol, Propylene Glycol (1,2 dihydroxy Propane), and Hydroxypropylcellulose NF 1500 CPS, but which did not contain DMSO, Echinaceas, or Arnica.

The greater effectiveness of the composition of the present teachings for reducing pain in the foot described in Tables 1-3 may be attributed to the fact that DMSO is a highly effective transdermal vehicle that allows for deep tissue penetration of the Lidocaine and anti-inflammatory agents, e.g., Echinaceas and Arnica.

Reduction in Pain and Reduction in Pain Score after topically treating foot pain for the test group listed in Table 4, infra, and after topically treating foot pain for the control group listed in Table 5, infra, show that the compositions described in Table 3, and by extrapolation in Tables 1-2, in which the only anesthetic is lidocaine, was more effective in reducing pain in the foot compared to a topical generic Lidocaine preparation. Lidocaine is the only anesthetic in the compositions used to topically treat foot pain for the test group listed in Table 4, infra. This is an improvement over compositions having lidocaine and/or other anesthetics such as tetracaine, since the use of co-administered local anesthetics' toxicity levels is thought to be at least additive.[2] When lidocaine and tetracaine is used concomitantly with other products containing local anesthetic agents, the amount absorbed from all formulations should be considered since the systemic toxic effects are thought to be additive and potentially synergistic with lidocaine and tetracaine.[3]

Surprisingly, 100% of plantar fasciitis patients reported significant pain reduction over a two-week period based on an Absolute Visual Analogue Scale (AVAS) as a Measure of Pain Intensity. The patients suffered significant foot pain caused by swelling or inflammation of fascia, ligaments or tendons, including pain due to plantar fasciitis on entering the trial. At the end of a two week study period, the average pain score reduction for the test group was 3.14 points (out of 10) also based on each foot (listed in Table 4, infra) counted as a trial if it had pain. Therefore, Table 4, infra, shows an average 60.8% reduction in pain scale for the test group from study initiation compared to the control group.

Surprisingly also the test group showed an average reduction of pain score of 3.14 points (out of 10).

At the end of a two week study, the average pain score reduction for the control group was 1 point (out of 10) also based on each foot (listed in Table 5, infra) counted as a trial if it had pain. Note patient 5 left foot actually increased in pain 1 point. In this comparator arm study, reduction in pain was less than 25% during the two-week comparative period.

TABLE 4

Investigator's Summary of Test Group Study Based on Reduction in Pain and Reduction in Pain Score (Using an Absolute Visual Analogue Scale (AVAS) as a Measure of Pain Intensity).

| PAIN BASELINE SUBJECT # | | After 1st Week | | After 2nd Week | | % CHANGE |
|---|---|---|---|---|---|---|
| SUBJECT 1 | | | NEUROPATHY, ARCH PAIN AND DIGITAL PAIN | | | |
| R | 3 | R | 1 | R | 1 | 66% REDUCED |
| L | 6 | L | 2 | L | 2 | 66% REDUCED |

"Working wonders on the middle left toe. I would say that if I apply the medicine three times a day the discomfort goes down to zero. I have gotten some noticeable relief on the left transverse arch which tends to be more painful."

| SUBJECT 2 | | | ARCH AND HEEL PAIN | | | |
|---|---|---|---|---|---|---|
| L | 7 | L | 4 | L | 2 | 65% REDUCED |

Note: Uses daily and is very pleased.
NOTE: Patient 2 had significant Plantar fasciitis and was included though some nueropathy was present.

| SUBJECT 3 | | | ARCH AND HEEL PAIN | | | |
|---|---|---|---|---|---|---|
| L | 8 | L | 4 | L | 2 | 75% REDUCED |

"Reduced pain in both feet, used 2x a day. Easy to use but takes 10 minutes to dry."

| SUBJECT 5 | | | ARCH AND HEEL PAIN | | | |
|---|---|---|---|---|---|---|
| R | 4 | R | 3 | R | 2 | 50% REDUCED |
| L | 2 | L | 1.5 | L | 2 | NO CHANGE |

Pain diminished immediately upon application Lasted for 1-2 hours. Diminished again at reapplication. Drying time was not a problem.
NOTE: Pain reduction while USING the product on left with no lasting change.

| SUBJECT 6 | | | LONG STANDING ARCH AND HEEL PAIN | | | |
|---|---|---|---|---|---|---|
| R | 8 | R | 7.5 | R | 7 | 12.5% REDUCED |

Week 1: "Doing a good job for about 6 hours the last 5 days. Only need to apply about 3x's. It's doing a good job with this product to make my foot feel better."
Week 2: "Overall this cream I did feel like it helped decrease the pain in my right tendon/right foot. Would be something I would consider buying, if it numbed and eased the pain."
NOTE: Patient records significant pain reduction while USING the product. Patient noted significant pain reduction which is inconsistent with baseline and final visit pain scores.

| SUBJECT 7 | | | ARCH AND FOREFOOT PAIN | | | |
|---|---|---|---|---|---|---|
| R | 6 | R | 5 | R | 3 | 50% REDUCED |
| L | 8 | L | 5 | L | 3 | 73% REDUCED |

NOTE: Patients were coming into the office for rehabilitation treatment which most likely effected the pain reduction during the test period but the patients indicate a definite noticeable positive pain reduction from the direct application of the composition of Table 3 that was separate and identifiable.

TESTS SUBJECTS FOR WHOM TREATMENT WAS CONTINUED AFTER 2 WEEK TRIAL

| SUBJECT 8 | | | ARCH AND FOREFOOT PAIN | | | |
|---|---|---|---|---|---|---|

White Female age 31.

| L | 7 | L | — | L | 4.5 | 36% REDUCED |
|---|---|---|---|---|---|---|
| SUBJECT 9 | | | SEVERE ARCH, HEEL AND FOREFOOT PAIN | | | |

Black Female age 52.

| R | 7 | R | — | R | 4.5 | 36% REDUCED |
|---|---|---|---|---|---|---|
| L | 7 | L | — | L | 4.5 | 36% REDUCED |

Note: Subject 4 included a diagnosis of Neuropathy in the study which was outside of the protocol design as the composition of Table 3 is not formulated to treat neuropathy. Patient 4 had significant neuropathy and was dropped from the analysis. Subject 6 recorded significant pain reduction while using the product. This was inconsistent with baseline and final visit pain scores and the subject was dropped from the analysis. Subject 10 never returned to the investigator's office and was dropped from the analysis.

TABLE 5

Investigator's Summary of Lidocaine (4%) Control Group Study Based on Reduction in Pain and Reduction in Pain Score (Using an Absolute Visual Analogue Scale (AVAS) as a Measure of Pain Intensity).

| SUBJECT # | BASELINE | | TEST 1 | | TEST 2 | | % CHANGE |
|---|---|---|---|---|---|---|---|
| SUBJECT 1 | | | BILATERAL ARCH PAIN | | | | |
| P.H. | R | 4 | R | 4 | R | 4 | 0% REDUCED |
| | L | 5 | L | 5 | L | 5 | 0% REDUCED |
| | Unfortunately did not help at all. Would not purchase. | | | | | | |
| SUBJECT 2 | | | RIGHT ARCH PAIN | | | | |
| C.P. | R | 5 | R | 2 | R | 1.5 | 66% REDUCED |
| | Also used immobilization at home with a support. | | | | | | |
| | Overall patient feels the topical did provide some temporary relief. | | | | | | |
| | She 'wishes' it would last longer. | | | | | | |
| SUBJECT 3 | | | RIGHT ARCH AND METATARSAL PAIN | | | | |
| J.D. | R | 6 | R | | R | 2 | 66% REDUCED |
| | Would purchase product. | | | | | | NO DATA |
| SUBJECT 4 | | | BILATERAL ARCH AND HEEL PAIN | | | | |
| J.T. | R | 3 | R | 2 | R | 2 | 33% REDUCED |
| | L | 4 | L | 3 | L | 3 | 25% REDUCED |
| | Would possibly consider purchasing. | | | | | | |
| SUBJECT 5 | | | BILATERAL ARCH AND HEEL PAIN | | | | |
| N.D. | R | 10 | R | 7 | R | 7 | 30% REDUCED |
| | L | 6 | L | 7 | L | 7 | 17 % WORSE |
| | NOTE: Would not purchase 4% Lidocaine product. | | | | | | |
| SUBJECT 6 | | | RIGHT ARCH AND HEEL PAIN LEFT LATERAL HEEL AND METATARSAL PAIN | | | | |
| J.J. | R | 6 | R | 5 | R | 5 | 17% REDUCED |
| | L | 4 | L | 3 | L | 3 | 25% REDUCED |
| | NOTE: Patient would possibly consider purchasing. | | | | | | |
| SUBJECT 7 | BILATERAL ARCH PAIN | | | | | | |
| T.J. | R | 5 | R | 3 | R | 2.5 | 50% REDUCED |
| | L | 5 | L | 3 | L | 2.5 | 50% REDUCED |
| | Would consider purchasing. | | | | | | |
| SUBJECT 8 | RIGHT ARCH AND MEDIAL FOREFOOT PAIN | | | | | | |
| J.C. | R | 4 | R | 4 | R | 4 | 0% REDUCED |
| | Would not purchase. | | | | | | |
| SUBJECT 9 | | | Moderate ARCH and HEEL pain | | | | |
| J.T. | R | 7 | R | 7 | R | 7 | 0% REDUCED |
| | Would not purchase. | | | | | | |
| SUBJECT 10 | | | Arch and forefoot pain and "itching" | | | | |
| S. W. | R/L | 7 | R/L | 7 | R/L | 7 | 0% REDUCED |
| | Liked first product more than 4% Lidocaine. | | | | | | |

The foregoing description of the embodiments of this invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of this invention as defined by the accompanying claims.

APPENDIX 1

1. Derry S1, Wiffen P J, Moore R A, Quinlan J. Cochrane, "Topical lidocaine for neuropathic pain in adults," *Database Syst Rev.* 2014 Jul. 24;7:CD010958. doi: 10.1002/14651858. CD010958. pub2.
2. Tina Alste, "Review of Lidocaine/Tetracaine Cream as a Topical Anesthetic for Dermatologic Laser Procedures", Pain Ther. 2013 Jun.; 2(1): 11-19. Published online 2013 Apr. 6. doi: 10.1007/s40122-013-0010-2.
3. Galderma USA. Pliaglis prescribing information. http://www.galdermausa.com/pdf/10156700-0407%20PLIAGLIS%20Package%20Insert.pdf. Accessed 19 Mar. 2013.

We claim:

1. A method for topically treating a condition causing pain due to swelling inflammation of fascia, tendons, or ligaments of a patient in need of treatment thereof, comprising:
   topically applying a pharmaceutically effective composition at ambient temperature to a patient in need of treatment thereof, the pharmaceutically effective composition consisting essentially of: In 100 parts by weight of the composition:

68.6-29.4 parts by weight of a pharmaceutically acceptable excipient;
40.0-50.0 parts by weight DMSO;
1.0-5.0 parts by weight of an anesthetic, wherein the anesthetic is characterized as containing only lidocaine; and
1.2-3.2 parts by weight of an anti-inflammatory.

2. The method of claim 1, wherein the pharmaceutically acceptable excipient is selected from the group of excipients consisting of DMSO, isopropyl alcohol, propylene glycol (PG), ethylene glycol (EG), polypropylene glycol (PPG), diethylene glycol monosubstituted ether (DGMSE), BHT, glycerin, propylene glycol, transcutol, triethanolamine, hydroxypropyl cellulose, nitrocellulose, hydroxypropyl cellulose (NF), hydroxypropyl cellulose (HPC), and combinations thereof.

3. The method of any one of the preceding claims, wherein the pharmaceutically acceptable excipient comprises 0.6-1.6 parts by weight hydroxypropyl cellulose NF, resulting in a viscosity of the composition being from about 18,000 cps to about 42,000 cps at 20° C.

4. The method of claim 2, wherein the anesthetic is in the range of 3.0 to 5.0 parts by weight Lidocaine.

5. The method of claim 2, wherein the pharmaceutically effective composition consists essentially of 48.0 parts by weight pharmaceutically acceptable excipient, 45 parts by weight DMSO, 4.0 parts by weight anesthetic, wherein the anesthetic is characterized as containing only lidocaine, and the anti-inflammatory ingredient is 1.0 part by weight Echinaceas, and 1.0 part by weight Arnica.

6. The method of claim 5, wherein the pharmaceutically acceptable excipient contains 1.0 part hydroxypropyl cellulose NF, resulting in a viscosity of the composition in a range of about 18,000 cps to about 42,000 cps at 20° C.

7. The method of claim 2, wherein the anti-inflammatory is selected from the group consisting of Echinacea, Arnica, and combinations thereof.

8. The method of claim 7, wherein the Echinacea and Arnica are each in the range 0.6 to 1.2 parts by weight in 100 parts by weight of the composition.

9. The method of claim 7, wherein the Echinacea and Arnica are each 1.0 part by weight in 100 parts by weight of the composition.

10. The method of claim 2, wherein the pain is caused by swelling or inflammation of the plantar fascia and the condition is Plantar Fasciitis.

11. The method of claim 2, where the pain is caused by swelling or inflammation of fascia, ligaments, or tendons of the foot and is selected from the group consisting of bilateral arch pain, right arch pain, right arch and metatarsal pain, bilateral arch and heel pain, right arch and heel pain, left lateral heel and metatarsal pain, right arch and medial forefoot pain, moderate arch and heel pain, arch and forefoot pain and itching.

* * * * *